US00PP33360P3

(12) United States Plant Patent
Sidhu

(10) Patent No.: US PP33,360 P3
(45) Date of Patent: Aug. 17, 2021

(54) THUJA TREE NAMED 'THUSID4'

(50) Latin Name: *Thuja occidentalis*
Varietal Denomination: Thusid4

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 0 days.

(21) Appl. No.: 17/001,505

(22) Filed: Aug. 24, 2020

(65) Prior Publication Data

US 2021/0084802 P1 Mar. 18, 2021

(30) Foreign Application Priority Data

Sep. 19, 2019 (CA) ..... 19-10006

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ... A01H 7/00; A01H 5/12; A01H 5/00; A01H 5/02; A01H 6/14
See application file for complete search history.

*Primary Examiner* — June Hwu
(74) *Attorney, Agent, or Firm* — Penny J. Aguirre

(57) ABSTRACT

A new cultivar of *Thuja occidentalis* Tree named 'Thusid4' characterized by its fine textured foliage that is green in color, its tight and compact growth habit, and its upright conical plant habit.

2 Drawing Sheets

CROSS-REFERENCE TO A RELATED APPLICATION

This application claims priority to a Canadian Plant Breeder's Rights Application No. 19-10006 filed on Sep. 19, 2019, under 35 U.S.C. 119(f), the entire contents of which is incorporated by reference herein.

Botanical classification: *Thuja occidentalis.*

Varietal denomination: 'Thusid4'.

BACKGROUND OF THE INVENTION

The present invention relates to a new and distinct cultivar of *Thuja occidentalis* and will be referred to hereafter by its cultivar name, 'Thusid4'. 'Thusid4' represents a new western red cedar, an evergreen tree grown for landscape use.

The inventor discovered 'Thusid4' as a naturally occurring branch mutation of *Thuja occidentalis* 'Smaragd' (not patented) in summer of 2015 that was growing outdoors in a container in a production block in Deroche, B.C., Canada.

Asexual propagation of the new cultivar was first accomplished by stem cuttings by the Inventor in February of 2016 in Mission, B.C., Canada. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Thusid4' as a unique cultivar of *Thuja.*

1. 'Thusid4' exhibits fine textured foliage that is green in color.
2. 'Thusid4' exhibits a tight and compact growth habit.
3. 'Thusid4' exhibits an upright conical plant habit.

'Smaragd', the parent plant of 'Thusid4', is similar to 'Thusid4' in foliage color and in having an upright plant habit. 'Smaragd', the parent plant of 'Thusid4', differs from 'Thusid4' in having a more vigorous growth habit, a less dense branching habit, a more narrow plant habit, and leaves that have a coarser texture (less fine). 'Thusid4' can be most closely compared to *Thuja occidentalis* 'Brandon' (not patented). 'Brandon' is similar to 'Thusid4' in having an upright plant habit. 'Brandon' differs from 'Thusid4' in having a more vigorous plant habit, a much less dense branching habit, and leaves that have a coarser texture (less fine) and darker green in color.

BRIEF DESCRIPTION OF THE DRAWINGS

The accompanying colored photographs illustrate the overall appearance and distinct characteristics of the new *Thuja.*

The photograph in FIG. 1 was taken of a 6-year-old tree as grown outdoors in a 4-liter container at a nursery in Mission, B.C., Canada and provides an overall view of the plant habit of 'Thusid4'.

Figure 1:
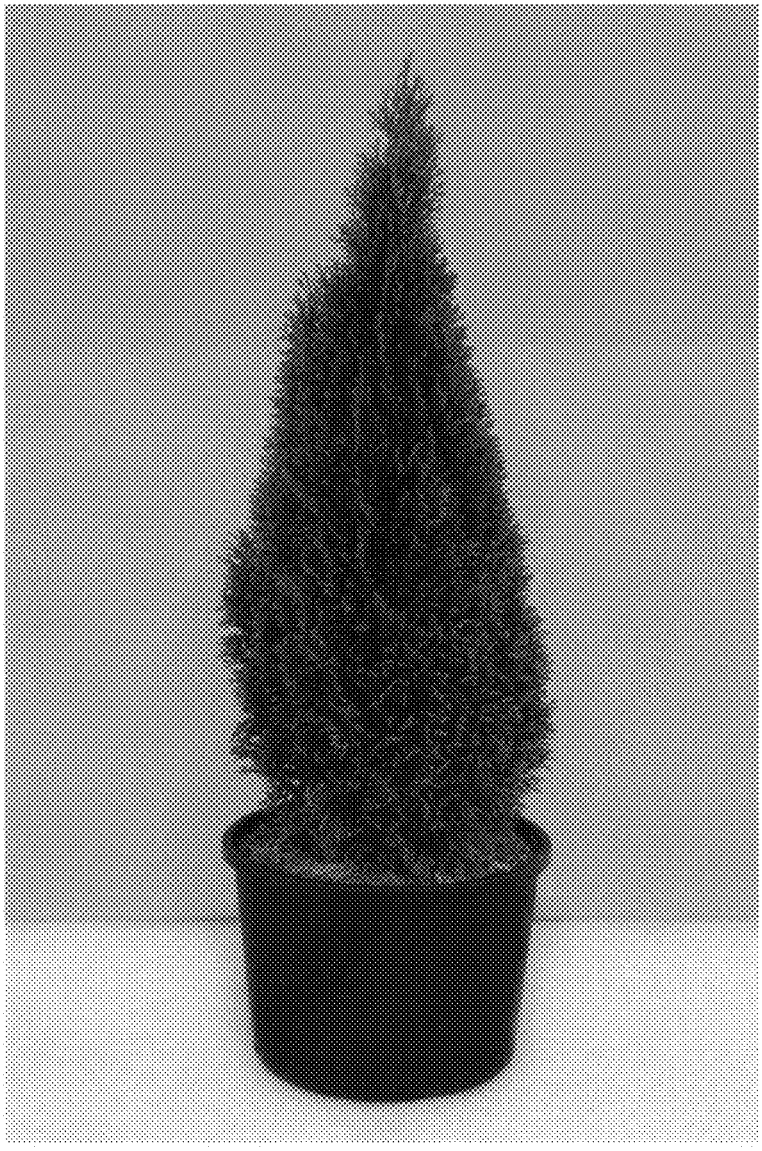
Figure 2:
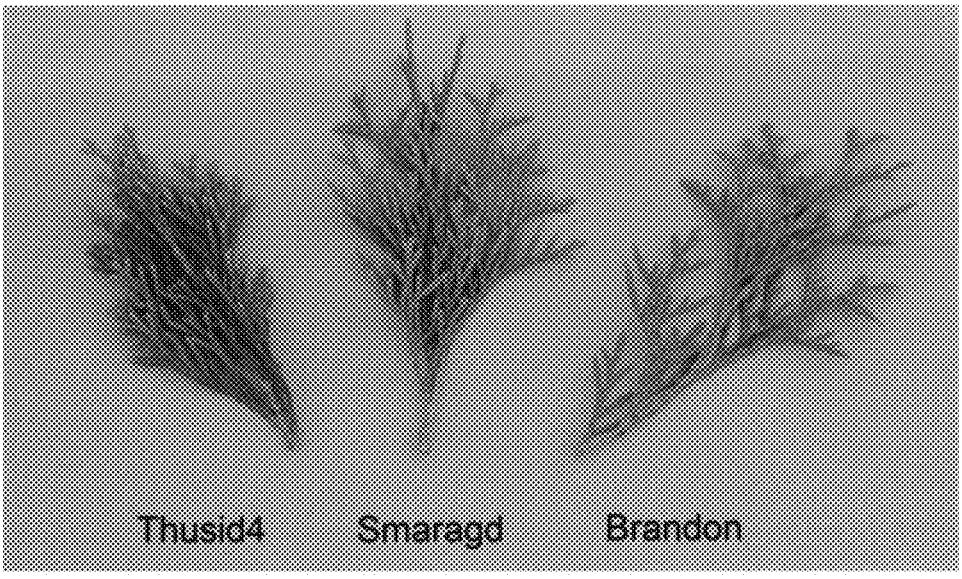
Figure 3:
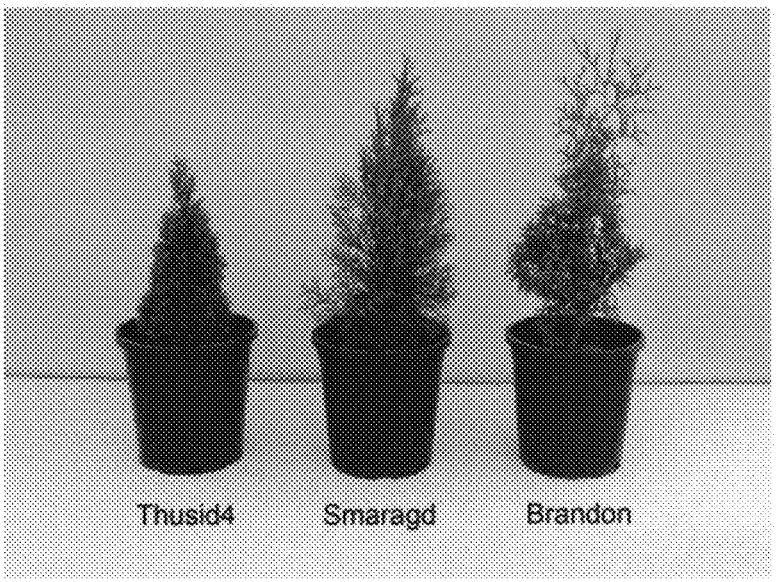

The photograph in FIG. 2 and FIG. 3 were taken of three-year-old trees of the new cultivar as grown in one-gallon containers in St. Thomas, Ontario, Canada.

The photograph in FIG. 2 provides a close-up view of sprays of 'Thusid4' (left) in comparison to 'Smaragd' (middle) and 'Brandon' (right).

The photograph in FIG. 3 provides a view of the plant habit of 'Thusid4' (left) in comparison to 'Smaragd' (middle) and 'Brandon' (right).

The colors in the photographs are as close as possible with the photographic and printing technology utilized. The color values cited in the detailed botanical description accurately describe the colors of the new *Thuja.*

DETAILED BOTANICAL DESCRIPTION

The following is a detailed description of the new cultivar of three-year-old trees of the new cultivar as grown in one-gallon containers in St. Thomas, Ontario, Canada. The phenotype of the new cultivar may vary with variations in environmental, climatic, and cultural conditions, as it has not been tested under all possible environmental conditions. The color determination is in accordance with The 2007 Colour Chart of The Royal Horticultural Society, London, England, except where general color terms of ordinary dictionary significance are used.

General description:

*Plant type.*—Evergreen tree.

*Plant habit.*—Upright, conical in shape, compact with fine foliage.

*Height and spread.*—An average of 42 cm in height and 18.5 cm in width as grown in a one-gallon container as a 3-years-old plant, a mature plant 7 years in age reaches an average of 1.83 m in height and 61 cm in width in the landscape.

*Cold hardiness.*—At least in U.S.D.A. Zones 3.

*Diseases and pests.*—No susceptibility or resistance to diseases or pests has been observed.

*Root description.*—Fibrous.

*Propagation.*—Stem cuttings.

*Root development.*—Time required for root initiation is 2 months, time required to produce a young plant from a rooted cutting is an average of 2 growing seasons to produce a 1-gallon container.

*Growth rate.*—Slow, 5 to 6 inches per year.

Branch description:

*Trunk.*—Woody, rough barked surface, close to 177A in color, about 1.2 cm in diameter at base.

*Branch shape.*—Rounded.

*Branch density.*—Very dense.

*Branch strength.*—Strong.

*Branch arrangement.*—Alternate.

*Branch attitude.*—Very erect.

*Number of branches.*—Average of 14.

*Branch, spray type.*—Flat.

*Branch, attitude of spray.*—Very upright.

*Branches.*—Woody, 177A to 177B in color, about 4 mm in diameter, spray size an average of 19.2 cm in length and 8.0 cm in width.

*Branch, internode length.*—Average 5 mm.

*Branchlets of first order.*—Average of 13, non-woody, 144A to 144C in color, about 2 mm in diameter, spray size an average of 8.7 cm in length and 5.1 cm in width.

*Branchlets of penultimate and last order.*—Non-woody, 144A to 144C in color, <2 mm in diameter, ranging from 1.0 cm to 4.4 cm in length.

*Branchlets of penultimate and last order.*—Non-variegated.

*Branchlets of penultimate and last order.*—Color in summer, upper surface closest to 138A, lower surface closest to 138B, new growth in summer, upper and lower side closest to 143C.

*Branch surface.*—Primary branches are woody, glabrous and knobby with scales (close to 164C in color).

Foliage description:

*Leaf arrangement.*—Numerous leaves arranged on planar scale-like decussate.

*Leaf shape.*—Facial pair keeled, flat pair flattened and oblong.

*Leaf division.*—Simple.

*Leaf base.*—Cuneate.

*Leaf apex.*—Apiculate.

*Leaf venation.*—Not visible.

*Leaf margins.*—Entire.

*Leaf surface.*—Upper and lower surface; glabrous, medium glossiness.

*Leaf color.*—New growth upper and lower surface 143C tinged with 174B, young growth upper surface; 143C, young growth lower surface; 143A to 143B, mature growth upper surface: closest to 138A; mature growth lower surface; 138B winter color upper and lower surfaces same as mature growth upper and lower surfaces.

*Leaf fragrance.*—Evergreen scent when crushed.

*Leaf size.*—An average of 3 mm in length and 1 mm in width.

Cone description: Neither male nor female cones have been observed to date.

It is claimed:

1. A new and distinct cultivar of *Thuja* tree named 'Thusid4' as herein illustrated and described.

* * * * *